US007791252B2

(12) United States Patent
Baumgartner et al.

(10) Patent No.: US 7,791,252 B2
(45) Date of Patent: Sep. 7, 2010

(54) ULTRASOUND PROBE ASSEMBLY AND METHOD OF FABRICATION

(75) Inventors: Charles Edward Baumgartner, Schenectady, NY (US); Robert Stephen Lewandowski, Amsterdam, NY (US); Kevin Matthew Durocher, Waterford, NY (US); David Chartrand, Mesa, AZ (US)

(73) Assignee: General Electric Company, Niskayuna, NY (US)

( * ) Notice: Subject to any disclaimer, the term of this patent is extended or adjusted under 35 U.S.C. 154(b) by 722 days.

(21) Appl. No.: 11/668,656

(22) Filed: Jan. 30, 2007

(65) Prior Publication Data
US 2008/0178677 A1 Jul. 31, 2008

(51) Int. Cl.
*H04R 17/00* (2006.01)
(52) U.S. Cl. .................. 310/334; 367/155; 367/157; 73/606
(58) Field of Classification Search ............... 310/334; 367/155, 157; 73/606
See application file for complete search history.

(56) References Cited

U.S. PATENT DOCUMENTS

| 6,292,433 B1* | 9/2001 | Gilbert et al. ............... 367/138 |
| 6,541,896 B1* | 4/2003 | Piel et al. ..................... 310/334 |
| 6,645,162 B2* | 11/2003 | Friedman et al. ............... 601/2 |
| 6,759,791 B2 | 7/2004 | Hatangadi |
| 6,761,688 B1* | 7/2004 | Mohr et al. .................. 600/437 |
| 6,822,376 B2 | 11/2004 | Baumgartner |
| 7,053,530 B2 | 5/2006 | Baumgartner |
| 2003/0073906 A1* | 4/2003 | Flesch et al. ................. 600/459 |
| 2003/0085635 A1* | 5/2003 | Davidsen ..................... 310/334 |
| 2005/0221633 A1* | 10/2005 | Wildes et al. .................. 439/67 |
| 2008/0106976 A1* | 5/2008 | Davidsen et al. ............. 367/140 |

* cited by examiner

*Primary Examiner*—Walter Benson
*Assistant Examiner*—Bryan P Gordon
(74) *Attorney, Agent, or Firm*—Scott J. Asmus (57) ABSTRACT

An ultrasonic imaging system wherein an exemplary system includes an array of transducer elements arranged along a first plane for transmitting first signals and receiving reflected signals for image processing. Circuit structures each have a major surface positioned in a co-planar orientation with respect to a major surface of another of the circuit structures to provide a sequence of the structures in a stack-like formation. Electrical connections are formed between adjacent circuit structures in the sequence. A connector region on each circuit structure includes a distal portion extending away from the major surface-with distal portions of connector regions of adjacent structures spaced apart from one another. A first wiring pattern extends from the major surface to the distal portion of the connector region. The plurality of circuit structures are configured to provide a second wiring pattern including at least some of the electrical connections formed between the circuit structures, extending from one or more of the first wiring patterns to multiple of the transducer elements.

16 Claims, 7 Drawing Sheets

ULTRASOUND PROBE ASSEMBLY AND METHOD OF FABRICATION

BACKGROUND OF THE INVENTION

1. Field of the Invention

This invention relates to ultrasonic imaging and, more particularly, to structures and methods forming electrical assemblies for acoustic sensors.

2. Background Art

In many ultrasound imaging systems, transducer element signals are generated in a hand-held probe unit and sent to a system console through a multi-channel cable system. In some of these systems a probe may utilize a relatively small array of 128 or 256 transducer elements with each element connected to the console via the cable system. Real time 3D ultrasound imaging systems may use larger 2D arrays of transducers. There are applications in which it is desirable for large ultrasound arrays to contain thousands or tens of thousands of transducer elements. With such a large number of elements, it becomes difficult to route individual connections between elements in a hand-held probe unit and electronics in the system console.

In medical imaging applications, this problem has been addressed, in part, by placing a limited portion of the processing circuitry in the probe unit instead of in the console. Some designs form the large array of transducer elements in subarrays, each perhaps containing 10 to 40 elements, and each subarray has a dedicated circuit unit providing part of the beamforming function. Each subarray circuit unit can transfer the signals from all of the transducer elements in the subarray to a single channel or wire, e.g., by analog beam formation, so that the signals for all of the elements in the subarray can be transferred via a single cable lead to the processing circuitry in the console. In this way thousands of signals can be carried on a more limited number of lines, resulting in a manageable cable size.

With continued increases in the size of transducer arrays in an ultrasound system, it is desirable to place even more processing electronics in the assembly housing. However, in medical applications requiring relatively small, light-weight hand-held probe units, it becomes more of a challenge to provide systems with higher resolution capability while meeting size and weight constraints.

Movement of more circuit functions into a hand-held probe unit can reduce the wire count at the interface between the probe unit and the cable assembly. This requires an extensive number of additional connections and routings among transducer elements and circuit elements which may be placed on multiple circuit boards. With the transducer array formed along a major plane, a large number of flexible circuit boards are each positioned with a major surface thereof in an orthogonal orientation relative to the major plane along which the transducer array is formed. In such a configuration, a transducer array having, for example, 64 rows of elements, can require connection with 64 individual flex circuits. Additional electronic components providing circuit functions such as pulse generation and beamforming may be connected to each of the individual flex circuits, resulting in a relatively large and complex assembly. Thus while increasing the sizes of image arrays, e.g., for purposes of increasing image resolution or field, there is, simultaneously, a need to further reduce the size, complexity and number of components in the electrical connection structure.

BRIEF DESCRIPTION

In accord with one embodiment of the invention, an ultrasonic imaging system includes an array of transducer elements and a plurality of circuit structures. The transducer elements are arranged in rows and columns along a first plane for transmitting and receiving signals. The circuit structures each include a major surface and a connector region extending away from the major surface. The major surfaces are positioned in a co-planar orientation with respect to one another to provide a sequence of the structures in a stack-like formation. Electrical connections are formed between adjacent circuit structures in the sequence. Along each circuit structure a first wiring pattern extends from each major surface to a distal portion of the connector region. The plurality of circuit structures is configured to provide a second wiring pattern extending from one or more of the first wiring patterns to multiple of the transducer elements.

In another embodiment of the invention, an ultrasonic probe includes a plurality of flexible circuits each including a first region and one or more connector regions extending away from each first region. First regions of different circuits are laminated to one another. Each first region includes a plurality of through vias. Through vias in different first regions are connected to provide electrical interconnection among the flexible circuits. Transducer elements in an array each have an electrical connection to at least one of the flexible circuits. A circuit board is connected to receive signals from one or more of the transducer elements through electrical traces formed on one or more of the flexible circuits. A cable provides electrical connections between the circuit board and beam forming circuitry in an associated system console.

A method is also provided for fabricating a flexible multilayer interconnection assembly for an ultrasonic probe. In one embodiment, a plurality of flexible circuits are provided with through-vias formed therein and electrical traces formed thereon. Portions of the circuits are bonded together and electrical connections between the bonded portions are formed. Each circuit further includes at least one non-bonded portion extending away from the bonded portion. An array of transducer elements is provided along a first plane. The array of transducer elements is attached to the circuits so that the circuits are oriented in planes parallel with the first plane. Electrical traces are formed along non-bonded portions of the flexible circuits and some of the electrical traces in individual ones of the flexible circuits are connected to a printed circuit board for processing signals received by an element in the array.

BRIEF DESCRIPTION OF THE DRAWINGS

The invention will be more clearly understood from the following description wherein an embodiment is illustrated, by way of example only, with reference to the accompanying drawings, in which.

Like reference numbers are used throughout the figures to indicate like features. Individual features in the figures may not be drawn to scale.

DETAILED DESCRIPTION OF THE INVENTION

In accordance with embodiments of the present invention, systems comprising interconnection assemblies and methods of forming interconnection assemblies are described herein. In the following detailed description, numerous specific details are set forth in order to provide a complete understanding of a context in which the present invention may be practiced. However, those skilled in the art will understand that embodiments of the present invention may be practices without these specific details and the invention is not limited to the disclosed embodiments.

Figure 1:
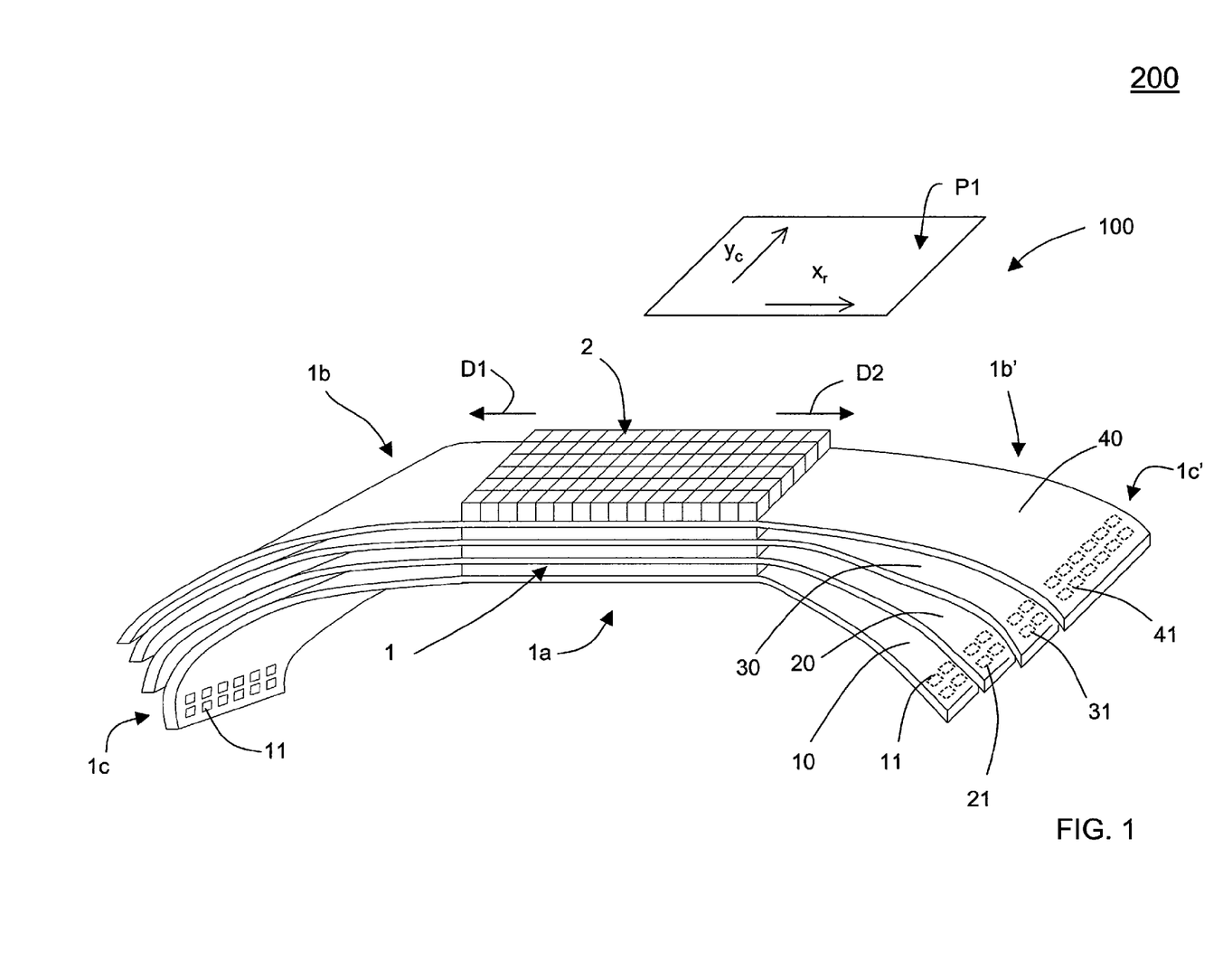
FIG. 1 illustrates a perspective view of a multilayer flex assembly.
Figure 2:
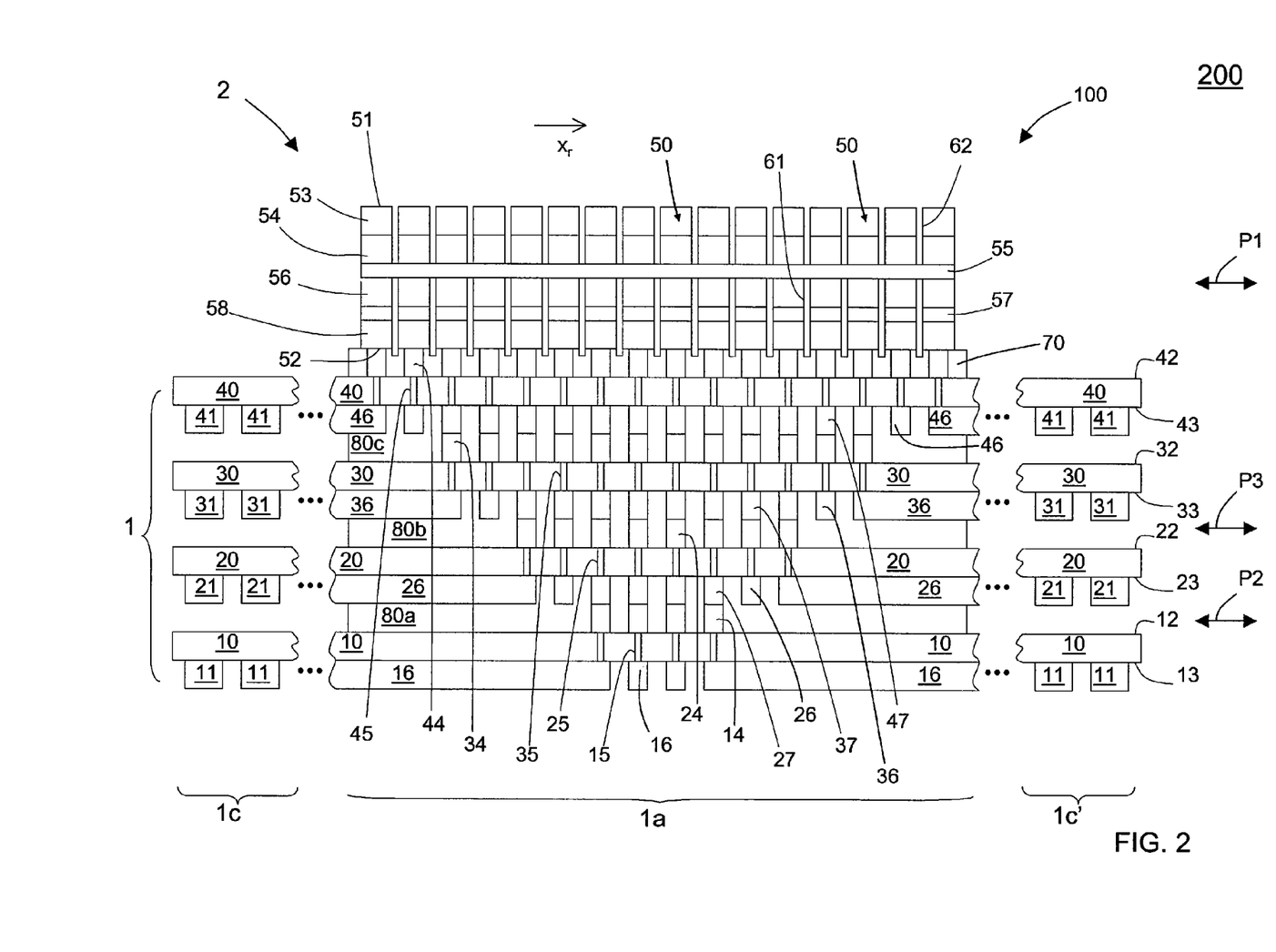
FIG. 2 illustrates a partial schematic cross-sectional view of the multilayer flex assembly of FIG. 1.

Referring now to the drawings, FIG. 1 provides a perspective view of a portion of a transducer circuit assembly 100 including a multilayer flexible circuit assembly 1 and a transducer array 2 in an ultrasonic imaging system 200. The array 2, comprising a large number of transducer elements 50, such as shown in the cross sectional view of FIG. 2, is formed about a plane P1, with the elements 50 arranged in rows $x_r$ and columns $y_c$. Although an upper surface of the array 2 is illustrated as co-planar with the plane P1, the array 2 may be curvilinear in shape about the plane P1. Rows xr of elements 50 extend along a first direction parallel with the plane P1, herein referred to as the x direction, and columns $y_c$ extend along a second direction parallel the plane P1 and orthogonal to the x direction. For purposes of illustrating features of example embodiments certain planes and features, including the plane P1, are referred to as having a horizontal orientation while other planes and features having an orthogonal orientation relative to a horizontal feature are described as having a vertical orientation.

Figure 3:
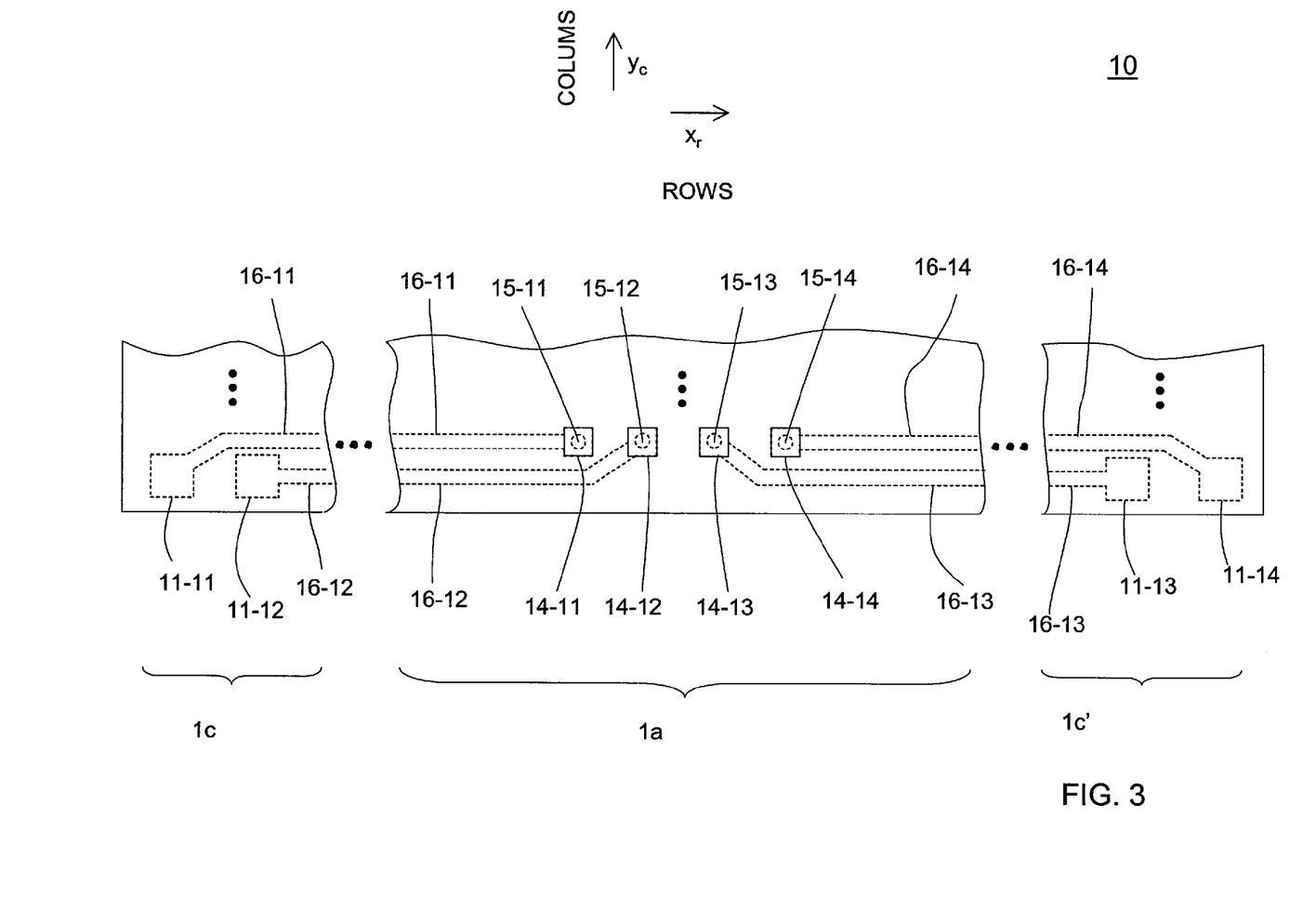
FIG. 3 illustrates a partial schematic plan view of a flex in the assembly of FIG. 1.
Figure 4:
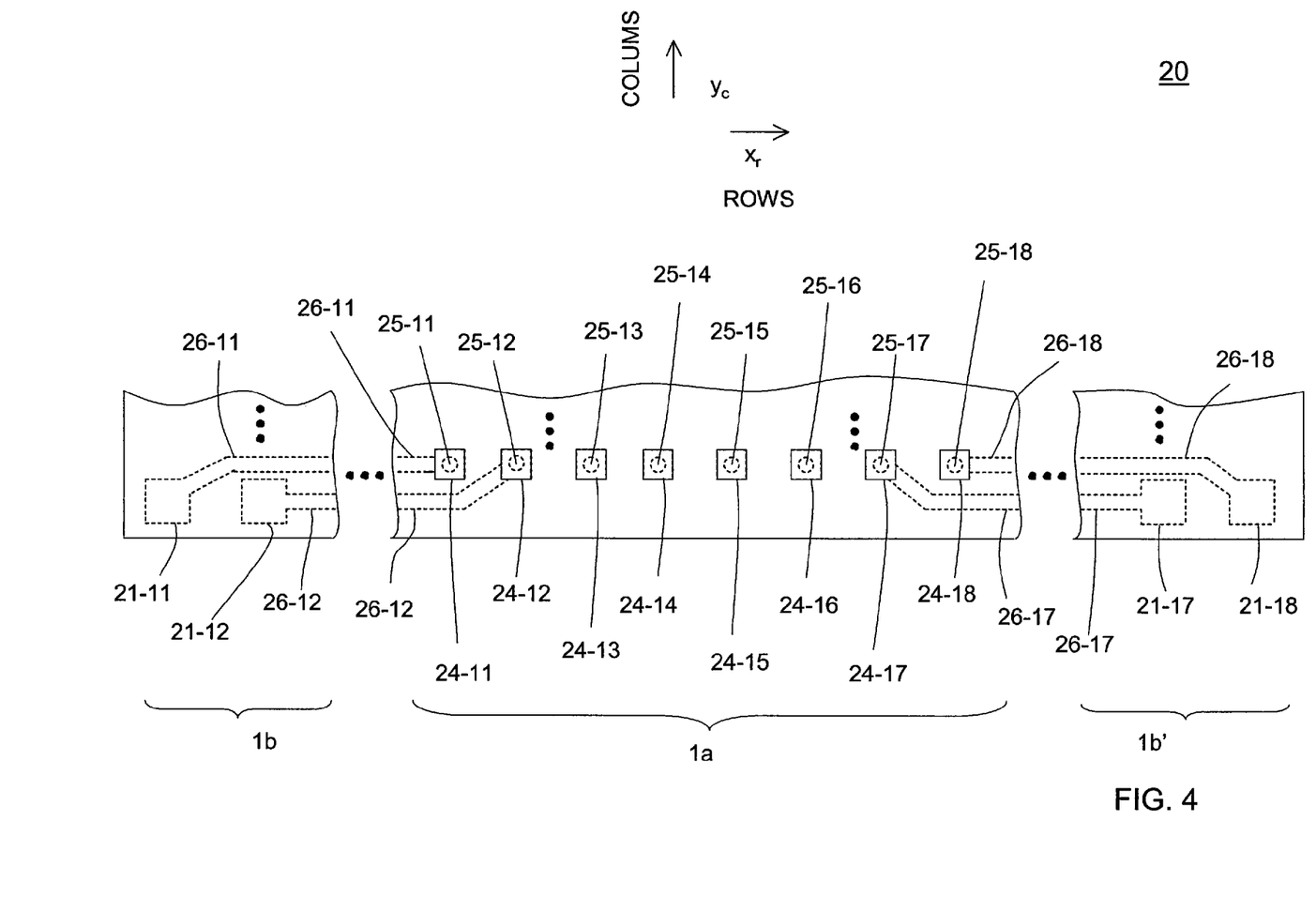
FIG. 4 illustrates a partial schematic plan view of another flex in the assembly of FIG. 1.

The flexible circuit assembly 1 comprises a large number of flexible circuit boards, herein referred to as "flexes", although, for simplicity of illustration, a sequence of only four flexes is shown in FIG. 1. A first flex 10 includes a series of first flex bond pads 11; a second flex 20 includes series of second flex bond pads 21; a third flex 30 includes a series of third flex bond pads 31; and a fourth flex 40 includes a series of fourth flex bond pads 41. All of the flexes are laminated to one another along a central major surface region 1a which is semi-rigid and positioned along the plane P1. First and second non-laminated regions 1b and 1b', herein referred to as connector regions, each extend away from the region 1a. Each of the connector regions 1b and 1b' includes a distal portion 1c and 1c', respectively. The distal portions 1c and 1c' on each flex extend in different directions D1 and D2, respectively, parallel with the x direction and outward from the central major surface region 1a. Each series of bond pads 11, 21, 31 and 41 is formed along edges of pairs of distal portions in one of the flexes. For example, the flex 10 includes bond pads 11 on a first distal portion 1c in the first connector region 1b and a bond pads 11 on a second distal portion 1c' in the second connector region 1b'. The bond pads in the distal portion 1c' are illustrated in phantom lines as they are formed on a lower surface of a flex. Although not shown in FIG. 1, each bond pad is connected to the central major surface region by a conductive trace such as shown in FIGS. 2, 3, and 4. Although not illustrated, the second connector regions 1b and 1b' may extend away from the laminated surface region 1a in other directions, e.g., the y direction.

Figure 6:
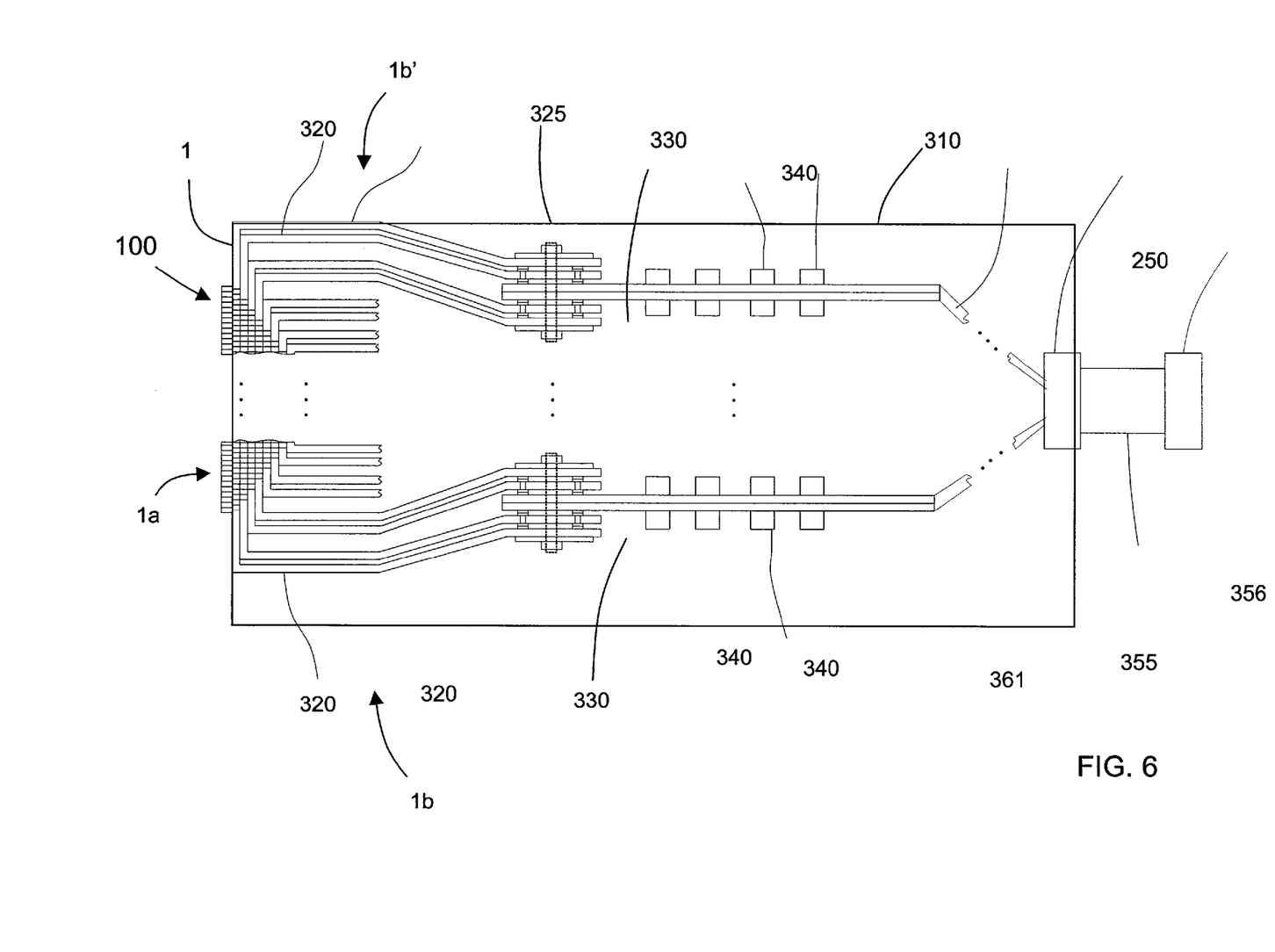
FIG. 6 is a cross-sectional view of a probe handle shown in FIG. 5.
Figure 7:
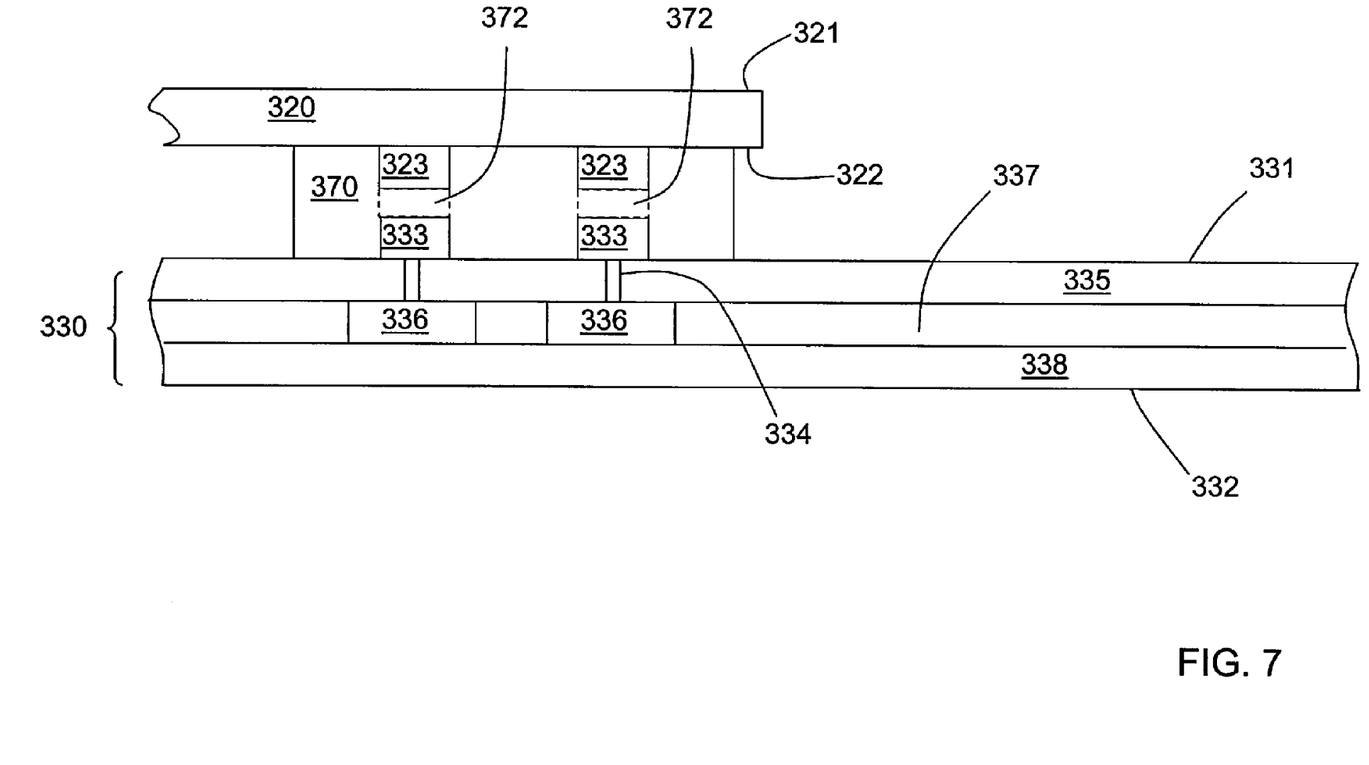
FIG. 7 is a partial schematic cross-sectional view illustrating connection between a flex and a printed circuit board.

In still other embodiments, more than two connector regions may be formed such that non-laminated regions extend in all directions from each semi-rigid laminated surface region 1a. With the major surface regions 1a of the flexes each having a horizontal orientation parallel to the plane P1, a series of substantially vertical electrical connection paths extends through the laminated major surface regions 1a to route signals between each of the transducer elements 50 and a bond pad on one of the flexes, such as a pad in the series of first flex bond pads 11. Although not illustrated in FIG. 1, bond pads along different edges of a flex are connectable to printed circuit boards (PCB's) such as shown in FIGS. 6 and 7. Probe electronic components mounted on PCB's (as described with reference to FIGS. 5 and 6) provide pulse generation and beamforming functions in association with related elements 50 of the transducer array 2. In other embodiments each of the series of flex bond pads 11, 21, 31, and 41 may be formed on an upper surface or both upper and lower surfaces of a flex.

FIG. 2 is a partial cross-sectional view of the multilayer flex assembly 100 of the ultrasound imaging system 200 having flex bond pads formed on the lower surfaces of the flexes, again illustrating four exemplary flexes 10, 20, 30 and 40 in a larger series of flexes. The view of FIG. 2 is taken along one of the rows $x_r$ of transducer elements 50 to illustrate an exemplary connection configuration between transducer elements 50 and electrical traces on the flexes 10, 20, 30, and 40.

The transducer array 2 is attached to the circuit assembly 1 with an adhesive 70. To effect electrical conduction between the circuit assembly 1 and the transducer array 2, the adhesive must be of the anisotropically conductive type or may be a non-conductive adhesive applied and then subjected to heat and pressure so that the adhesive is displaced as electrical surfaces formed of noble metal such as gold come into contact with one another. Alternately, electrical connection between the circuit assembly 1 and the transducer array 2 may be had with solder balls or "chip on flex".

The transducer elements 50 each having an upper surface 51 and a lower surface 52 include a first matching layer 53 along the upper surface 51, a second matching layer 54 adjoining the first matching layer 53, a front ground electrode 55 positioned between the matching layer 54 and a piezoelectric material layer 56, a rear or signal electrode 57 positioned between the layer 56 and an electrically conductive dematching layer 58. The signal electrode 57 may be formed by depositing metal on the piezoelectric material layer 56 before laminating the piezoelectric material layer 56 to the dematching layer 58. Spacings or kerfs are formed to electrically isolate the piezoelectric elements 50 in adjacent rows and columns from one another. For example, the kerfs 61 may be formed in vertical planes relative to the horizontal plane P1 by sawing through the layers 56, 57, and 58. Subsequently, the electrode 55 is formed as a continuous conductive layer over the elements 50 to provide a common ground. The electrode 55 may be a thin metal layer (e.g., 0.25-4 microns) formed on the second matching layer 54 by an electroplating technique and laminated to the piezoelectric layer 56. The first matching layer 53 may be laminated to the second matching layer 54 so that both layers 53 and 54 are sawed along the same vertical planes as the piezoelectric layer is sawed, thereby forming kerfs 62 vertically aligned with the kerfs 61. The sawing of the matching layer 54 stops short of the ground metallization 55.

In this way the transducer elements 50 are acoustically separated from one another, but electrically connected via the ground metallization.

The multilayer flex circuit assembly 1 is formed by laminating the central major surface regions 1a of adjoining flexes, e.g., the flexes 10, 20, 30, and 40 to one another in a coplanar orientation with non-conductive adhesive sheets 80 cut to approximately the length and width dimensions (along the x and y directions) of the major surface regions 1a. Each sheet (e.g., 80a, 80b, 80c) is placed between two adjacent flexes with mating contact pads of adjacent flexes aligned to one another. Each contact pad has a contact surface formed of a noble metal such as gold. Thicknesses of the adhesive sheets 80 are generally in the range of 0.010 mm-0.100 mm, sufficient for making electrical contacts without damaging the mating contact pad pairs. The dimensions of the adhesive sheets 80 along the directions of the plane P1 are the same as or slightly smaller than those of the transducer array. The mating flex contact pads on individual flex circuits become electrically connected to one another when heat and pressure are applied in the vertical direction along the regions 1a as excess epoxy is squeezed from these areas. This produces a sequence of flexes in a stack-like formation with electrical connections between adjacent flexes in the sequence. See U.S. Ser. No. 11,560,867 titled "Electronic System With Lead Free Interconnections and Method of Fabrication", filed Nov. 17, 2006, assigned to the assignee of the present invention and incorporated herein by reference.

The first flex 10 having an upper surface 12 and a lower surface 13, includes four upper contact pads 14 (herein referred to as first flex upper contact pads 14), four through-flex conductive vias 15 formed in the major surface region 1a (herein referred to as first flex vias 15), four electrical traces 16 formed on the lower surface 13 (herein referred to as first flex traces 16), and four first flex bond pads 11. Two of the four bond pads 11 are formed in each of the distal regions 1c and 1c'. Each first flex trace 16 connects a first flex via 15 and a corresponding one of the first flex bond pads 11. The second flex 20 having an upper surface 22 and a lower surface 23, includes eight upper contact pads 24 (herein referred to as second flex upper contact pads 24), eight through-flex conductive vias 25 (herein referred to as second flex vias 25), four electrical traces 26 formed on the lower surface 23 (herein referred to as second flex traces 26), four second flex bond pads 21 (two of the bond pads 21 formed in each distal region 1c and 1c'), and four lower contact pads 27, herein referred as second flex lower contact pads 27. Each second flex trace 26 connects a second flex via 25 and a corresponding second flex bond pad 21.

The third flex 30 having an upper surface 32 and a lower surface 33, includes twelve upper contact pads 34 (herein referred to as third flex upper contact pads 34), twelve through-flex conductive vias 35 (herein referred to as third flex vias 35), four electrical traces 36 formed on the lower surface 33 (herein referred to as third flex traces 36), four third flex bond pads 31 (with two of the bond pads 31 formed in each distal region 1c and 1c'), and eight lower contact pads 37, herein referred to as third flex lower contact pads 37. Each third flex trace 36 connects a third flex via 35 and a corresponding third flex bond pad 31. The fourth flex 40 having an upper surface 42 and a lower surface 43, includes sixteen upper contact pads 44 (herein referred as fourth flex upper contact pads 44), sixteen through-flex vias 45 (herein referred as fourth flex vias 45), four electrical traces 46 formed on the lower surface 43 (herein referred as fourth flex traces 46), four fourth flex bond pads 41 (with two of the bond pads 41 formed in each distal region 1c and 1c'), and twelve fourth flex lower contact pads 47. Each fourth flex trace 46 connects a fourth flex via 45 and a corresponding fourth flex bond pad 41.

The adhesive layer 80a provides an adhesive bond between the first flex 10 and the second flex 20. The adhesive layer 80b provides an adhesive bond between the second flex 20 and the third flex 30. The adhesive layer 80c provides an adhesive bond between the third flex 30 and the fourth flex 40. In other embodiments, electrical contacts between flexes may be formed using anisotropically conductive adhesives with heat and compression, soldering, bumping, or other common methods.

Still referring to FIG. 2, each transducer element in each row $x_r$ is connected to a fourth flex via 45 through a layer 59 in FIG. 2 does not exist. Instead, dematching layer 58 is bonded directly onto the top flex circuit 40 to make connection to the bond pads on the top of layer 40 and the upper fourth flex contact pads 44. The two flex vias 45 connected to the elements 50 in the two columns $y_c$ closest to the first distal portion 1c and the two flex vias 45 connected to the elements 50 in the two columns $y_c$ closest to the second distal portion 1c' are connected through fourth flex traces 46 to fourth flex bond pads 41 formed along the lower surface 43 of the fourth flex 40 in the distal region 1c. With respect to four columns of elements 50, associated columns of fourth flex vias 45 and associated fourth flex traces 46 effect connection of two columns of elements 50 to the first distal portion 1c and effect connection of two columns of elements 50 to the second distal portion 1c', forming a first wiring pattern. Other columns $y_c$ of fourth flex vias 45 (i.e., other than those contacting fourth flex bond pads 41) are connected through the fourth flex lower contact pads 47 to the third flex upper contact pads 34. The third flex upper contact pads 34 provide electrical connections between those of the fourth flex vias 45 not connected to portions 1c and 1c' through the traces 41 and the third flex vias 35 of the flex 30, forming a second wiring pattern.

With reference to the flex 30, the third flex vias 35, connected to the elements 50 in the two columns $y_c$ closest to the first distal portion 1c, are connected through third flex traces 36 to third flex bond pads 31 formed along the lower surface 33 on the distal portion 1c of the flex 30. Similarly, the third flex vias 35, connected to the elements 50 in the two columns $y_c$ closest to the second distal portion 1c' of the flex 30 are connected through third flex traces 36 to third flex bond pads 31 formed along the lower surface 33 on the second distal portion 1c' of the flex 30. With respect to four columns of elements 50, associated columns of third flex vias 35 and associated third flex traces 36 effect connection of two columns of elements 50 to bond pads 31 in the first distal portion 1c of the flex 30 and effect connection of two columns of elements 50 to bond pads 31 in the second distal portion 1c' of the flex 30. The second flex upper contact pads 24 formed on the upper surface 22 of the flex 20 provide electrical connections for those of the third flex vias 35 not connected to bond pads 31 on the flex 30 through the traces 36. These connections are made through third flex lower contact pads 37, second flex upper contact pads 24 and second flex vias 25 of the flex 20 to the second flex bond pads 21 and the first flex bond pads 11.

With reference to the flex 20, the second flex vias 25, connected to the elements 50 in the two columns $y_c$ closest to the first distal portion 1c, are connected through second flex traces 26 to second flex bond pads 21 formed along the lower surface 23 on the distal portion 1c of the flex 20. The second flex vias 25, connected to the elements 50 in the two columns $y_c$ closest to the second distal portion 1c' of the flex 20 are similarly connected through second flex traces 26 to second flex bond pads 21 on the second distal portion 1c' of the flex 20. With respect to four columns of elements 50, associated columns of second flex vias 25 and associated second flex traces 26 effect connection of two columns of elements 50 to bond pads 21 in the first distal portion 1c of the flex 20 and effect connection of two columns of elements 50 to bond pads 21 in the second distal portion 1c' of the flex 20. The first flex upper contact pads 14 provide electrical connections for those of the second flex vias 25 not connected to portions 1c and 1c' of the flex 20 through the traces 26. These connections are made through the second flex lower contact pads 27 and the first flex vias 15 of the flex 10 to the first flex bond pads 11.

With reference to the flex 10, the first flex vias 15, connected to the elements 50 in the two columns $y_c$ closest to the first distal portion 1c, are connected through first flex traces 16 to first flex bond pads 11 formed along the upper surface 12 on the distal portion 1c of the flex 10. Similarly, the first flex vias 15, connected to the elements 50 in the two columns $y_c$ closest to the second distal portion 1c', are connected through first flex traces 16 to first flex bond pads 11 formed along the lower surface 13 on the second distal portion 1c' of the flex 10. With respect to four columns of elements 50, associated columns of first flex vias 15 and associated first flex traces 16 effect connection of two columns of elements 50 to bond pads 11 in the first distal portion 1c of the flex 10 and effect connection of two columns of elements 50 to bond pads 11 in the second distal portion 1c' of the flex 10.

Understanding that that the assembly 100 contains a larger number of flexes than the illustrated four flexes, the flex 10 may include additional first flex upper contact pads (not shown), to provide electrical connections for additional flex vias 15 (not illustrated) which are not connected to bond pads 11. These connections are made through additional contact pads (not shown) formed on the lower surface 13 of the flex 10 and the flex vias of another flex (not shown) positioned in the sequence containing the flexes 40, 30, 20 and 10, and following the flex 10. The above-described interconnect configuration continues with additional flexes in the sequence in order to route connections in all of the columns $y_c$ to bond pads along distal portions 1c and 1c' on other flexes in the sequence for further connection to other circuit components such as printed circuit boards.

Stacked vias formed in each major surface region 1a and associated electrical traces extending to distal portions in the same flex provide electrical connections between individual transducer elements 50 and a corresponding bond pad in the flex. Electrical connections between individual transducer elements 50 and a corresponding fourth flex bond pad 41 are provided by the fourth flex via 45 and fourth flex traces 46. Electrical connections between individual transducer elements 50 and a corresponding third flex bond pad 31 are provided by vertical alignment and interconnection between third flex vias 35, fourth flex vias 45, and third flex traces 36. Electrical connections between individual transducer elements 50 and a corresponding second flex bond pad 21 are provided by vertical alignment and interconnection between second flex vias 25, third flex vias 35, fourth flex vias 45, and second flex traces 26. Electrical connections between individual transducer elements 50 and a corresponding first flex bond pad 11 are provided by vertical alignment and interconnection between first flex vias 15, the second flex vias 25, the third flex vias 35, the fourth flex via 45, and first flex traces 16.

In FIGS. 3 and 4 electrical connections between individual flex vias and corresponding bond pads in the first flex 10 and the second flex 20 are described in plan views. FIG. 3 is a partial plan view of the first flex 10 taken along a second plane P2 parallel to the first plane P1 (as shown in FIG. 2), and through the first flex upper contact pads 14. Components shown in phantom lines are above or below the plane P2. FIG. 3 illustrates several flex vias 15 in a first row (along the $x_r$ direction) of such vias, indicated as 15-11, 15-12, 15-13, 15-14, each connected with one of the first flex traces 16, indicated as 16-11, 16-12, 16-13, and 16-14, to effect connection with corresponding bond pads 11, indicated as 11-11 and 11-12 in the first distal region 1c and 11-13 and 11-14 in the second distal region 12c'. By way of example, the connection between the upper first flex contact pad 14-11 and the corresponding first flex bond pad 11-11 comprises the pad 14-11 connected to the first flex via 15-11, connected to a first flex trace 16-11, connected to the first flex bond pad 11-11.

FIG. 4 is a partial plan view of the second flex 20 taken along the plane P3 (shown in FIG. 2), which is parallel with the planes P1 and P2, and through the second flex upper contact pads 24. Components shown in phantom lines are above or below the plane P3. In FIG. 4 the second flex vias 25-11 and 25-12 with lower second flex contact pads 24-11, 24-12 are connected to the corresponding second flex bond pads 21-11 and 21-12 in the first distal region 1b by the second flex traces 26-11 and 26-12, respectively. The second flex vias 25-17 and 25-18 are connected to the corresponding second flex bond pads 21-17 and 21-18 in the second distal region 1b' by the first flex traces 26-17 and 26-18, respectively. By way of further illustration, the connection between an upper second flex contact pad 24-11 and the corresponding second flex bond pad 21-11 comprises the pad 24-11 connected to the first flex via 25-11, connected to the second flex trace 26-11, connected to the second flex bond pad 21-11. The four second flex vias 25-13, 25-14, 25-15, and 25-16 are connected to the corresponding lower second flex contact pads 24-13, 24-14, 24-14, 24-15, 24-16 which are connected to the upper first flex contact pads 14-11, 14-12, 14-13, and 14-14 in FIG. 3 for connection to the first flex bond pads 11-11, 11-12, 11-13, and 11-14 via the first flex traces 16-11, 16-12, 16-13, and 16-14 as already described with regard to FIG. 3.

Figure 5:
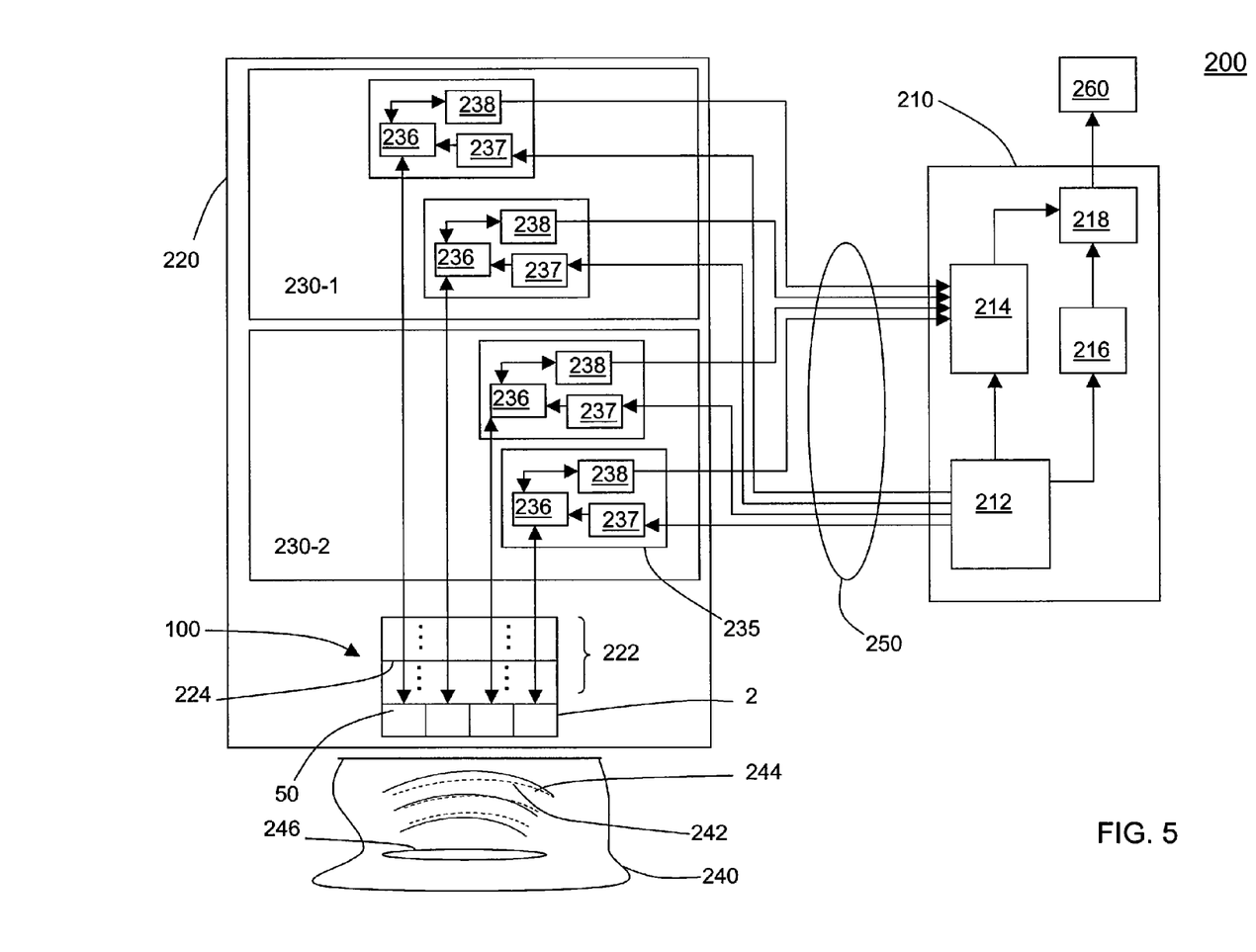
FIG. 5 illustrates an exemplary imaging system incorporating an embodiment of the invention.

FIG. 5 is a simplified block diagram of the ultrasonic imaging system 200 including a system console 210, connected to a probe unit 220 by a cable bundle 250, and a display 260. The probe unit 220 includes the multilayer flex transducer assembly 100, configured in accord with the example shown in FIGS. 1-4. A partial view of the assembly 100 is shown, having a stack 222 of flexes 224, such as the flexes 10, 20, 30 and 40 shown in FIG. 2 and an array 2 of transducer elements 50, such as illustrated in FIG. 2. One exemplary flex 224 and four columns of transducer elements 50 are shown in this simplified schematic view, which is taken along the direction of a row $x_r$. It is to be understood that, for the embodiment of FIGS. 1-4, the stack 222 will include a large number of flexes 224, each connected to a number of columns $y_c$ of elements 50. Each flex 224 transfers input and output signals between elements 50 in several columns $y_c$ (see FIGS. 2-4) and multiple ones of the probe electronics units 235. Each unit 235 provides signal processing and control functions to a column $y_c$ of transducer elements 50 and includes a transmitter/receiver switch 236, transmitter circuitry 237, and receiver circuitry 238. Signals from the exemplary flex 224 connected to the first two transducer columns $y_c$ are transferred to two probe electronics units 235 mounted on a first printed circuit board 230-1 and signals from the exemplary flex 224 connected to the last two columns $y_c$ are transferred to two probe electronics units mounted on a second printed circuit board 230-2. Signal processing performed in a probe electronics unit 235, referred to as probe beamforming, can reduce the number of cables required in the cable bundle 250 when a multiplexing/demultiplexing algorithm is employed in the probe beamforming circuitry.

The system console 210 includes a system controller 212, main beamforming circuitry 214, an image processor 216, and a scan converter 218. The system controller 212 is coupled to the main beamformer 214, the image processor 216, and a plurality of transmitters 237 of the probe electronics 235 on the PCB 230 to provide necessary timing signals to each of the various devices. In operation of the system 200, each transmitter 237 provides electronic transmit signals to a transducer element 50 which converts the electrical signals to ultrasonic pressure waves herein illustrated by ultrasound lines 242. A portion of the transmitted energy may return to the array as reflections 244 after interacting at boundaries of a feature 246 on an object 240 having an abrupt transition in acoustic impedance.

FIG. 6 further illustrates an exemplary application of the embodiment shown in FIGS. 1-5. A probe unit 310 of the ultrasound imaging system 200 is shown containing the multilayer flex transducer assembly 100 having a plurality of flexes 320, a plurality of Printed Circuit Boards (PCBs) 330 each containing a plurality of probe electronics units 340, Flexible connectors 361 carry signals between the PCBs 330 and a cable connector 355. The connector 355 receives a mating connector 356 in which individual wires of a cable bundle 250 terminate to effect connection to circuitry (such as the main beamformer 214 illustrated in FIG. 5) in the system console 210.

The exemplary flex circuit assembly 1 includes a major surface region 1a and a first connector region 1b and a second connector region 1b'. The connector regions 1b and 1b' of individual flexes 320 in the circuit assembly 1 are each connected to a corresponding Printed Circuit Board (PCB) 330. In other embodiments, the flexes 320 may be attached to semi-rigid Flexible Circuit Boards (FCBs). The connector regions 1b and 1b' may be joined with the PCBs 330 by a clamp 325 as illustrated in FIG. 6. The electronic components 340 can be mounted directly onto the flex circuits with the circuit routing made to the individual electronic components via flex traces.

FIG. 7 illustrates another wiring configuration for the probe unit 310. A flex 320 and a PCB 330 are bonded together with an anisotropically conducting film (ACF) 370 to provide a multilayer flex transducer assembly having a plurality of flexes 320 and a plurality of Printed Circuit Boards (PCBs) 330. The flex 320, having an upper surface 321 and a lower surface 322, includes a plurality of flex bond pads 323 formed along the lower surface 322. The PCB 330 includes an upper dielectric layer 335 formed over an intralevel dielectric layer 337 formed over a lower dielectric layer 338. The upper dielectric layer includes an upper surface 331 and a lower surface 332, and comprises a plurality of PCB contact pads 333 formed on the upper surface 331. Upper level vias 334 are formed in the upper level dielectric layer 335. Underlying inner conductors 336 are formed in the intra-level dielectric layer 337. Electrical conductors 372 are formed between the flex bond pads 323 and the PCB contact pads 333 when heat and pressure are applied to the anisotropically conducting film 370. In other embodiments, electrical contacts between the flexes and the PCBs may be formed by soldering, or with other common methods.

A structure has been illustrated for connecting electronic components to an array of transducer elements and a low cost process has been illustrated for producing the structure. In the past, connection of an array of transducer elements has provided signals to and from one entire row or column of the array through a single flex. Flex costs increase as the trace pitch decreases, and overall cost per flex increases as the number of elements connected to one flex increases. However, a significant savings in overall cost can be realized based on a net reduction in the number of flexes required to process signals associated with the entire array.

While various embodiments of the invention have been illustrated and described, the invention is not so limited. Numerous modifications, variations, substitutions and equivalents will occur to those skilled in the art without departing from the spirit and scope of the present invention as described in the claims.

The invention claimed is:

1. An ultrasonic imaging system comprising:
   an array of transducer elements arranged in rows and columns along a first plane for transmitting first signals and receiving reflected signals for image processing; and a plurality of circuit structures each having
   (a) a major surface positioned in a co-planar orientation with respect to a major surface of another of the circuit structures to provide a sequence of the structures in a stack-like formation wherein electrical connections are formed between adjacent circuit structures in the sequence, and wherein the major surfaces are each positioned along a plane substantially parallel with the first plane,
   (b) a connector region having a distal portion extending away from the major surface, with distal portions of connector regions of adjacent structures spaced apart from one another, and
   (c) a first wiring pattern extending from the major surface to the distal portion of the connector region,
   the plurality of circuit structures configured to provide a second wiring pattern, including at least some of the electrical connections formed between the circuit structures, extending from one or more of the first wiring patterns to multiple of the transducer elements, wherein two or more rows and/or two or more columns of said array are electrically connected to at least one of said first wiring pattern and said second wiring pattern.

2. The imaging system of claim 1 wherein each of the circuit structures is a flexible circuit board, and major surfaces of adjacent structures are bonded to one another, forming a relatively rigid portion in the sequence relative to the spaced apart distal portions.

3. The imaging system of claim 1 wherein the electrical connections between two of the adjacent circuit structures include conductive vias formed in each of the structures and contact pads formed along surfaces of the two structures facing one another with pads on the facing surfaces connected to one another thereby effecting connection between vias formed in the different structures.

4. The ultrasonic imaging system of claim 1 wherein:
   each major surface of a circuit structure is along a central portion of the circuit structure and each circuit structure includes at least two connector regions, each having a distal portion extending away from the major surface, a first of the distal portions extending away from the major surface along a first direction and a second of the distal portions extending away from the major surface in a direction different than the first direction,
   with distal portions of adjacent connector regions extending away from the major surface in the first direction spaced apart from one another and distal portions of adjacent connector regions extending away from the major surface in the second direction spaced apart from one another.

5. The system of claim 4 wherein a first of the structures is positioned closest to the array relative to a second of the structures and is configured to:

receive electrical signals from transducer elements in all of the columns in the array;

provide electrical signals from transducer elements in a first plurality of the columns in the array to the first connector region distal portion of the first structure forming the first wiring pattern;

provide electrical signals from transducer elements in a second plurality of the columns in the array to the second connector region distal portion of the first structure forming the second wiring pattern; and provide electrical signals from transducer elements in a third plurality of the columns in the array to the second of the structures forming the third wiring pattern.

6. The system of claim 5 wherein the second of the structures is configured to:

receive electrical signals from the transducer elements in the third plurality of columns;

provide electrical signals from the transducer elements in one or more first columns in the third plurality of columns to at least the first and second distal portions of the second structure; and provide electrical signals from the transducer elements in one or more second columns in the third plurality of columns to a third of the structures.

7. The system of claim 1 wherein a first of the structures is positioned closest to the array relative to a second of the structures and is configured to:

receive electrical signals from transducer elements in all of the columns in the array;

provide electrical signals from transducer elements in a first plurality of the columns to the distal portion of the connector region of the first structure; and provide electrical signals from transducer elements in a second plurality of the columns to the second of the structures.

8. The system of claim 7 wherein the second of the structures is configured to:

receive electrical signals from transducer elements in the second plurality of columns;

provide electrical signals from transducer elements in one or more first columns of the third plurality of columns to the distal portion of the connector region of second structure; and provide electrical signals from transducer elements in one or more second columns in the third plurality of columns to a third of the structures.

9. The system of claim 1 further including a system console housing beam forming circuitry, wherein the array of transducer elements and the plurality of circuit structures are housed in a probe unit which further includes:

a probe electronics unit;

a circuit board providing electrical connection between one of the circuit structures and the probe electronics unit; and a wiring cable providing electrical connections between the circuit board and an electronic component in a remote system console.

10. The system of claim 1 further including a system console housing beam forming circuitry, wherein the array of transducer elements and the plurality of circuit structures are housed in a probe unit which further includes:

a plurality of probe electronics units each electrically coupled to receive signals through a circuit structure;

a wiring cable providing electrical connections between the probe electronics units and one or more electronic components in the system console.

11. The system of claim 1 wherein the circuit structures are formed on flexible circuit boards.

12. The system of claim 1 further including a circuit board comprising electronics coupled to one or more of the circuit structures to switch a transducer element between transmit and receive modes, and provide signal processing and control functions.

13. The system of claim 1 wherein the major surfaces of the circuit structures form a laminate structure with adhesive between adjacent ones of the major surfaces.

14. The system of claim 1 wherein the array of transducer elements includes a common ground electrode, matching layers, piezoelectric material, signal electrodes, and a dematching layer.

15. An ultrasonic probe handle comprising:

a plurality of flexible circuits each including first region and one or more connector regions extending away from each first region, with first regions of different circuits laminated to one another, each first region including a plurality of through vias in different first regions connected to provide electrical interconnection among the flexible circuits;

an array of transducer elements arranged in rows and columns, each having an electrical connection to at least one of the flexible circuits, wherein the array of transducer elements is formed along a first plane and each of the flexible circuits is formed along a plane parallel with the first plane, wherein two or more rows and/or two or more columns of said array are electrically connected to the flexible circuits by at least one of a first wiring pattern and a second wiring pattern;

a circuit board connected to receive signals from one or more of the transducer elements through electrical traces formed on one or more of the flexible circuits;

a console housing beam forming circuitry; and a cable providing electrical connections between the circuit board and the beam forming circuitry in the system console.

16. The system of claim 14 wherein the circuit board is directly connected to one of the flexible circuits.

* * * * *

UNITED STATES PATENT AND TRADEMARK OFFICE
CERTIFICATE OF CORRECTION

PATENT NO. : 7,791,252 B2
APPLICATION NO. : 11/668656
DATED : September 7, 2010
INVENTOR(S) : Baumgartner et al.

It is certified that error appears in the above-identified patent and that said Letters Patent is hereby corrected as shown below:

On the Cover Page, item (57), under "ABSTRACT", in Column 2, Line 11, delete "surface-with" and insert -- surface, with --, therefor.

In Column 3, Line 32, delete "xr" and insert -- $x_r$ --, therefor.

In Column 8, Lines 31-32, delete "24-14, 24-14," and insert -- 24-14, --, therefor.

In Column 9, Line 20, delete "340," and insert -- 340. --, therefor.

In Column 12, Line 51, in Claim 16, delete "claim 14" and insert -- claim 15 --, therefor.

Signed and Sealed this

Sixteenth Day of November, 2010

David J. Kappos
*Director of the United States Patent and Trademark Office*